US 7,455,831 B2

(12) United States Patent
Vicic et al.

(10) Patent No.: US 7,455,831 B2
(45) Date of Patent: *Nov. 25, 2008

(54) NAIL VARNISH

(75) Inventors: Marco Vicic, Bry S/Marne (FR); Colette Cazeneuve, Paris (FR); Nathalie Mougin, Paris (FR)

(73) Assignee: L'Oreal S.A., Paris (FR)

(*) Notice: Subject to any disclaimer, the term of this patent is extended or adjusted under 35 U.S.C. 154(b) by 536 days.

This patent is subject to a terminal disclaimer.

(21) Appl. No.: 10/612,916

(22) Filed: Jul. 7, 2003

(65) Prior Publication Data

US 2004/0071643 A1 Apr. 15, 2004

Related U.S. Application Data

(60) Provisional application No. 60/401,027, filed on Aug. 6, 2002.

(30) Foreign Application Priority Data

Jul. 8, 2002 (FR) .................................. 02 08556

(51) Int. Cl.
*A61Q 3/00* (2006.01)
*A61Q 3/02* (2006.01)

(52) U.S. Cl. .......................................... 424/61; 424/401

(58) Field of Classification Search ................. 424/401, 424/61

See application file for complete search history.

(56) References Cited

U.S. PATENT DOCUMENTS 5,681,550 A 10/1997 Rubino
6,113,925 A * 9/2000 de la Poterie ................ 424/401
2004/0071644 A1* 4/2004 Mougin et al. ................ 424/61

FOREIGN PATENT DOCUMENTS

| EP | 0 658 609 | 6/1995 |
| EP | 0 898 958 B1 | 3/1999 |
| EP | 0 898 960 B1 | 3/1999 |
| FR | 2 814 674 A1 | 4/2002 |
| FR | 2 819 176 A1 | 7/2002 |
| WO | WO 02 39962 | 5/2002 |

OTHER PUBLICATIONS

J.M. Buist et al., "Advances in Polyurethane Technology," p. 286, pp. 296-297, 1968.
H.F. Mark et al., "Encyclopedia of polymer science and engineering," 2$^{nd}$ Ed. vol. 13, pp. 294-296.
English language Derwent Abstract of EP 0 898 958 B1.
English language Derwent Abstract of EP 0 898 960 B1.
English language Derwent Abstract of FR 2 819 176 A1.
English language Derwent Abstract of FR 2 814 674 A1.
French Search Report for FR 02/08556, Examiner Glikman, Apr. 11, 2003.

* cited by examiner

*Primary Examiner*—Johann Richter
*Assistant Examiner*—Konata M. George
(74) *Attorney, Agent, or Firm*—Finnegan, Henderson, Farabow, Garrett & Dunner, LLP

(57) ABSTRACT

Disclosed herein is a nail varnish composition comprising, in a cosmetically acceptable medium, at least one film-forming polymer, wherein the varnish composition is capable of forming a film having a rate of mass loss of less than 0.5 mg/minute when the film is subjected to abrasion produced with the Taber abrasimeter at 23° C., as well as a method for making up and/or non-therapeutic care of the nails comprising applying to the nails the composition.

47 Claims, No Drawings

NAIL VARNISH

This application claims benefit of U.S. Provisional Application No. 60/401,027, filed Aug. 6, 2002.

Disclosed herein is a nail varnish composition comprising at least one film-forming polymer having good staying power properties. Further disclosed herein is a method for making up and/or caring for nails.

The nail varnish composition may be used as a varnish base, as a make-up product for the nails, as a finishing composition, also called top coat, to be applied over the make-up product for the nails, and/or as a cosmetic care product for the nails. The nail varnish composition may be applied to the nails of human beings or to false nails.

The nail varnish compositions comprise, in a known manner, a film-forming polymer in an organic solvent medium or an aqueous medium. The varnish composition can form, after drying, a colored or colorless film on the nails and thus can make it possible to beautify or protect the nails against external attacks such as rubbing or scratches. However, known nail varnishes may frequently exhibit poor staying power over time: the film deteriorates, such as through flaking or detachment, after one or two days. Such a deterioration often occurs at the tip of the nail. When the varnish is damaged, the user then needs to remove the damaged varnish and then carry out another application of the varnish. The user can also touch up the damaged varnish by partially applying the varnish; but this type of touching up may not lead to a perfectly aesthetic make-up. If the user does nothing, the damaged varnish can impair the aesthetic appearance of the make-up and may not give good protection to the nail.

Other nail varnishes such as easily peelable varnishes or water-removable varnishes may not confer a good staying power over time either.

A need therefore exists to obtain novel nail varnishes, which can make it possible to obtain a film deposited on the nails having a satisfactory staying power over time, without exhibiting an unaesthetic defect.

As disclosed herein, a novel nail varnish composition is provided, which can have at least one good staying power property over time, such as good resistance to rubbing, to water and to flaking.

The inventors have discovered that a nail varnish exhibiting a low rate of mass loss during abrasion could make it possible to obtain a varnish having a good staying power over time.

Disclosed herein is a nail varnish composition comprising, in a cosmetically acceptable medium, at least one film-forming polymer, wherein the varnish composition is capable of forming a film having a rate of mass loss of less than 0.5 mg/minute when the film is subjected to abrasion produced with the Taber abrasimeter at 23° C. The nail varnish composition may further comprise at least one organic solvent.

Further disclosed herein is a cosmetic method for making up and/or non-therapeutic care of the nails, comprising applying to the nails at least one layer of the nail varnish composition as defined above.

As disclosed herein, the expression "film-forming polymer" means a polymer capable of forming, on its own, or in the presence of a film-forming aid, a continuous and adherent film on the nail, at a temperature ranging from 20° C. to 30° C.

The rate of mass loss from the nail varnish film is measured according to the protocol described below.

A layer of the composition is deposited on a metal (steel) support in order to obtain, after drying for 24 hours at 23±2° C. and at 55±5% relative humidity, a film having a thickness of about 100 µm (after drying). The film is subjected to abrasion for 60 minutes using a Taber abrasimeter (reference 5130 Abraser) provided with two abrasive wheels sold under the name CS10F by the company Taber Industries and by applying to each wheel a force of 2.5 N. During the abrasion operation, the rate of mass loss from the film is measured over a period of 60 minutes.

The nail varnish film disclosed herein can have a rate of mass loss of less than 0.5 mg/minute, such as less than 0.2 mg/minute, and further such as less than 0.1 mg/minute.

In addition, the nail varnish film can have a loss of gloss, after 10 seconds of abrasion with the Taber abrasimeter described above, of less than or equal to 14%, such as less than or equal to 12%, further such as less than or equal to 10%, and even further such as less than 6%. The loss of gloss corresponds to the (Bo−B)/Bo ratio in %, in which B represents the gloss of the film 1 hour after the abrasion and Bo represents the gloss of the film before the abrasion. The gloss of the film is measured with the aid of a Byk-Gardner gloss meter at a light beam angle of 60°.

In one embodiment, the at least one film-forming polymer has at least a glass transition temperature (Tg) ranging from −150° C. to 0° C., such as from −80° C. to 0° C.

The at least one film-forming polymer may also have an additional glass transition temperature of greater than 0° C. and less than or equal to 150° C., such as ranging from 10° C. to 100° C.

The measurement of the glass transition temperature (Tg) of the polymer is carried out by DMTA (Dynamical and Mechanical Temperature Analysis) as described below.

To measure the glass transition temperature (Tg) of the polymer, viscoelasticimetry tests are carried out using a DMTA apparatus from Polymer TA Instruments (model DMA2980), on a sample of polymer film about 150±50 µm thick, 5 mm wide and 10 mm long, after drying for 24 hours at 23±2° C. and 50-55% relative humidity. A tensile stress is applied to this sample. The sample is subjected to a static force of 0.01 N on which is superposed a sinusoidal displacement of ±8 µm at the frequency of 1 Hz. The work is thus done in the linear domain, at low deformation levels. This tensile stress is applied to the sample at temperatures varying from −150° C. to +220° C., with a temperature variation of 3° C. per minute.

The complex modulus $E^*=E'+iE''$ of the test polymer is then measured as a function of the temperature.

The dynamic storage modulus E' and the dynamic loss modulus E'', and the damping power: $tg\delta = E''/E'$, are obtained from these measurements.

A curve of the tgδ values as a function of the temperature is then collated; this curve has at least one peak. The glass transition temperature Tg of the polymer corresponds to the temperature at which the summit of this peak is located.

When the curve has at least 2 peaks (in this case, the polymer has at least 2 Tg), the temperature for which the curve has the peak with the highest amplitude (i.e., corresponding to the highest tgδ value; in this case, only the "predominant" Tg is considered as Tg value for the test polymer) is taken as Tg value for the test polymer.

In one embodiment, the nail varnish disclosed herein is capable of forming a film having a Young's modulus ranging from 10 to 200 MPa, such as ranging from 10 to 100 MPa, and further such as ranging from 10 to 50 MPa.

The mechanical properties of the nail varnish film is measured under monotonic tensile stress according to the STM Standards, volume 06.01 D 2370-92 "Standard Test Method for Tensile Properties of Organic Coatings". A test piece is cut from a free film having a thickness of 150±50 µm obtained after drying for 48 hours at 23±2° C. and 55±5% relative humidity a nail varnish layer deposited on a Teflon template. The test piece is dumb-bell-shaped, has a useful length of 33 mm and a useful width of 6 mm. The section (s) of the test piece is then defined as: s=width×thickness (mm$^2$); and this section (s) will be used to calculate the stress.

The tests are carried out on a tensile strength apparatus equipped with an optical extensometer for measurement of the displacement and marketed under the name Zwick Z010. The measurements are carried out under the same temperature and humidity conditions as for the drying, i.e., at a temperature of 23±2° C. and a relative humidity of 55±5%. The test pieces are pulled at a rate of displacement of 50 mm/min.

A rate of displacement is therefore imposed and the length (L) of the test piece and the force (f) necessary to impose this length are therefore simultaneously measured. The length (L) is measured with an optical extensometer using adhesive pads placed on the dumb-bell-shaped test piece. The initial distance between these two pads defines the useful length Lo used to calculate the strain $\epsilon=(L/Lo)\times 100$ expressed as %.

A stress curve $\sigma(=f/s)$ is thus obtained as a function of the strain $\epsilon$, the test being carried out until the test piece breaks.

The Young's modulus (modulus of elasticity), expressed in MPa, corresponds to the slope of the curve $\sigma=f(\epsilon)$, considered in the initial part of the curve (beginning of the test).

In one embodiment, the nail varnish disclosed herein is capable of forming a film having an energy at break, i.e., a fracture energy, $W_r$ ranging from $220\times 10^5$ to $1,000\times 10^5$ J/m$^3$, such as ranging from $240\times 10^5$ to $1,000\times 10^5$ J/m$^3$.

The energy at break (the fracture energy) $W_r$ expressed in J/m$^3$ corresponds to the area under the stress curve as a function of the strain; the area is defined by the relationship:

$$Wr = \left(\left(\int_0^{l\,max} f\,dl\right)\middle/(s\cdot Lo)\right)$$

in which:
f means the force applied to the film test piece;
s means the section of the film test piece;
Lo means the initial length of the film test piece before its strain; and
lmax is the maximum length of the test piece at the end of the pulling phase.

In one embodiment, the nail varnish disclosed herein is capable of forming a film having a breaking strain $\epsilon_r$ ranging from 300 to 2 000%, such as ranging from 500 to 2 000%. The breaking strain $\epsilon_r$ is the maximum strain of the sample before breakpoint (as %).

For example, the at least one film-forming polymer can be insoluble in water at 25° C., i.e., it is soluble at less than 1% by weight in water at 25° C. (solubility of less than 1% by weight). The at least one film-forming polymer can also, for example, be soluble at 25° C. in at least one organic solvent, such as ethyl acetate and methyl acetate, i.e., it is soluble greater than 90% by weight in at least one organic solvent at 25° C. (solubility greater than 90% by weight at 25° C.).

The at least one film-forming polymer has, for example, a number-average molecular weight of less than or equal to 300,000, such as ranging from 10,000 to 150,000.

The at least one film-forming polymer which makes it possible to obtain the varnish abrasion resistance properties may be chosen from free-radical polymers and polycondensates. For example, the at least one film-forming polymer is noncrosslinked.

For example, the at least one film-forming polymer may be chosen from polycondensates chosen, for example, from polyurethanes, polyureas, polyurea-urethanes, and mixtures thereof.

The polycondensates are, for example, chosen from those formed by polycondensation:
of at least one diisocyanate chosen from linear and branched $C_1$-$C_{12}$, such as $C_1$-$C_6$, alkyl diisocyanates, $C_4$-$C_{20}$ cycloalkyl diisocyanates, and $C_6$-$C_{20}$ aryl diisocyanates;
of at least one prepolymer comprising at least two functional groups comprising at least one labile hydrogen, such as a diol and primary and secondary diamines, having a number-average molecular mass ranging from 500 to 50,000, such as from 500 to 8,000, and further such as from 1,000 to 3,000; and
of at least one coupler comprising two functional groups comprising at least one labile hydrogen, such as a diol, primary and secondary diamines, and an amino alcohol, having a molecular mass of less than 500, such as greater than or equal to 50 and less than 500, and further such as greater than or equal to 75 and less than 500.

The at least one diisocyanate may be, for example, chosen from hexamethylene diisocyanate, isophorone diisocyanate, dicyclohexylmethane diisocyanate, toluene diisocyanate, diphenylmethane diisocyanate, dicyclohexylmethane diisocyanate, and tetramethylxylylene diisocyanate.

The at least one prepolymer described above may be, for example, chosen from (poly(tetramethylene oxide))diols comprising from 10 to 80 tetramethylene oxide units; polydimethylsiloxanes comprising at least one end group chosen from ($C_2$-$C_8$)alkylene-amino($C_2$-$C_8$)alkyl groups and $C_2$-$C_8$ ω-hydroxyalkyl groups; and hydrogenated polybutadienes comprising at least one hydroxyl end group.

The at least one coupler is, for example, chosen from diols, such as diols comprising from 4 to 12 carbon atoms, for example, from 4 to 8 carbon atoms. The at least one coupler may also be, for example, chosen from butanediol, neopentyl glycol, amino ethanol, propylene glycol, ethylene glycol, diethylene glycol, triethylene glycol and cyclohexanedimethanol.

The at least one prepolymer is, for example, non watersoluble, i.e., the at least one prepolymer has a water-solubility of less than 1% by weight, at 25° C.

For example, the at least one prepolymer and the at least one coupler described above are present in the at least one film-forming polymer, such as polyurethane, in an amount such that the prepolymer/coupler molar ratio ranges from 1:1 to 1:5 and the (prepolymer+coupler)/diisocyanate molar ratio ranges from 0.9:1 to 1.1:1.

When the (prepolymer+coupler)/diisocyanate molar ratio is less than 1, the free isocyanate groups are blocked by reaction with at least one compound comprising at least one labile hydrogen, such as ethanol.

For example, the at least one film-forming polymer is such that the prepolymer, the diisocyanate and the coupler are present in the polymer in the following molar proportion:
Prepolymer: 1;
Diisocyanate: from 2 to 6; and
Coupler: from 1 to 5.

The at least one film-forming polymer may be present in the nail varnish composition in an amount ranging from 0.1% to 60% by weight, relative to the total weight of the composition, such as from 0.1% to 40% by weight, relative to the total weight of the composition.

The nail varnish disclosed herein may further comprise at least one additional film-forming polymer, commonly called resin, such as sulphonamide resins, alkyd resins, cellulose esters such as cellulose acetobutyrate, cellulose acetate, cellulose acetopropionate.

The at least one additional film-forming polymer may be present in an amount ranging from 0.01% to 50% by weight, relative to the total weight of the composition, such as from 1% to 30% by weight, relative to the total weight of the composition.

The nail varnish composition disclosed herein may comprise at least one film-forming aid for improving the film-forming properties of the varnish.

The at least one film-forming aid may be chosen from any compounds known by persons skilled in the art to be capable of fulfilling the desired function, such as those chosen from plasticizing agents.

The plasticizing agents may be chosen, for example, from:
citrates such as triethyl citrate, tributyl citrate, triethyl acetylcitrate, tributyl acetylcitrate, and 2-triethylhexyl acetylcitrate;
phthalates such as diethyl phthalate, dibutyl phthalate, dioctyl phthalate, dipentyl phthalate, and dimethoxyethyl phthalate;
tricresyl phosphate, benzyl benzoate, tributyl phosphate, butyl acetylricinoleate, glyceryl acetylricinoleate, butyl glycolate, tributoxyethyl phosphate, triphenyl phosphate, dibutyl tartrate, camphor, glyceryl triacetate, N-ethyl-o,p-toluenesulphonamide, and mixtures thereof.

The at least one film-forming aid, such as the plasticizing agent, may be present in the composition in an amount ranging from 0.01% to 10% by weight, relative to the total weight of the composition, such as ranging from 0.1% to 5% by weight, relative to the total weight of the composition. For example, the plasticizer is present in the composition in a film-forming polymer/plasticizer weight ratio ranging from 1.5:1 to 3:1.

The composition disclosed herein may comprise an aqueous medium or an organic solvent medium. In one embodiment, an organic solvent medium is used. It may be, for example, anhydrous.

The aqueous medium of the composition comprises water. The water content in the composition may range from 10% to 95% by weight, relative to the total weight of the composition, such as from 40% to 90% by weight, and further such as from 60% to 85% by weight, relative to the total weight of the composition.

The varnish composition may also comprise at least one water-miscible solvent chosen, for example, from lower monoalcohols having from 1 to 5 carbon atoms, glycols having from 2 to 8 carbon atoms, $C_3$-$C_4$ ketones, $C_2$-$C_4$ aldehydes, such as in an amount ranging from 0.1% to 15% by weight, relative to the total weight of the composition.

When the varnish composition comprises an aqueous medium, the film-forming polymer is present in the form of solid particles dispersed in the aqueous medium. Such a dispersion is known by the name of latex or pseudolatex and may be prepared according to techniques well known to persons skilled in the art.

The organic solvent medium of the composition may comprise at least one organic solvent chosen, for example, from:
ketones which are liquid at room temperature, such as methyl ethyl ketone, methyl isobutyl ketone, diisobutyl ketone, isophorone, cyclohexanone, and acetone;
alcohols which are liquid at room temperature, such as ethanol, isopropanol, n-propanol, n-butanol, diacetone alcohol, 2-butoxyethanol, and cyclohexanol;
glycols which are liquid at room temperature, such as ethylene glycol, propylene glycol, pentylene glycol, and glycerol;
propylene glycol ethers which are liquid at room temperature, such as propylene glycol monomethyl ether, propylene glycol monomethyl ether acetate, and dipropylene glycol mono-n-butyl ether;
short-chain esters (having from 3 to 8 carbon atoms in total) such as ethyl acetate, methyl acetate, propyl acetate, n-butyl acetate, and isopentyl acetate;
ethers which are liquid at room temperature, such as diethyl ether, dimethyl ether, and dichlorodiethyl ether;
alkanes which are liquid at room temperature such as decane, heptane, dodecane, isododecane, and cyclohexane;
aromatic cyclic compounds which are liquid at room temperature, such as toluene and xylene; and
aldehydes which are liquid at room temperature, such as benzaldehyde and acetaldehyde.

The content of the at least one organic solvent in the composition may range, for example, from 10% to 95% by weight, relative to the total weight of the composition, such as from 40% to 90% by weight, and further such as from 60% to 85% by weight, relative to the total weight of the composition.

The varnish composition may comprise at least one thickening agent, for example, to confer on the composition a consistency allowing good application of the composition to the nails. The at least one thickening agent is, for example, an organic solvent thickener and may be chosen from hydrophobic silicas, such as those described in the document EP-A-898960, and for example marketed under the references "AEROSIL R812®" by the company Degussa, "CAB-O-SIL TS-530®", "CAB-O-SIL TS-610®", "CAB-O-SIL TS-720®" by the company Cabot, "AEROSIL R972®", "AEROSIL R974®" by the company Degussa; clays such as montmorillonite, stearalkonium hectorite, and stearalkonium bentonite; alkyl ethers of polysaccharides (such as those whose alkyl group comprises from 1 to 24 carbon atoms, such as from 1 to 10, and further such as from 1 to 6, and even further such as from 1 to 3 carbon atoms) such as those described in the document EP-A-898958, and for example marketed under the names "N-HANCE-AG 200®" and "N-HANCE AG 50®" by the company Aqualon.

The at least one thickening agent may be present in the composition disclosed herein in an amount ranging from 0.05% to 10% by weight, relative to the total weight of the composition, such as from 0.1% to 3% by weight, relative to the total weight of the composition.

The composition may also comprise at least one coloring matter chosen from fat-soluble colorants, pigments, pearlescent agents and glitter.

The fat-soluble colorants may be, for example, chosen from Sudan red, DC Red 17, DC Green 6, β-carotene, soybean oil, Sudan brown, DC Yellow 11, DC Violet 2, DC Orange 5, and quinoline yellow. The fat-soluble colorants may be present in the composition in an amount ranging from 0.01% to 6% by weight, relative to the total weight of the composition, such as from 0.01% to 3% by weight, relative to the total weight of the composition.

The at least one coloring matter chosen from pigments, pearlescent agents and glitter may be present in the composition, such as the base and/or top composition, in an amount ranging from 0.01% to 25% by weight, relative to the weight of the composition, such as from 0.01% to 15% by weight, relative to the total weight of the composition. The pigments can be chosen from inorganic pigments and organic pigments. The inorganic pigments may be chosen, for example, from titanium, zirconium and cerium oxides, and zinc, iron and chromium oxides and ferric blue. The organic pigments may be chosen, for example, from carbon black, barium, strontium, calcium and aluminium lacquers. Among the pearlescent agents, mica coated with titanium oxide, with iron oxide, with a natural pigment or with bismuth oxychloride, such as colored mica-titanium, may, for example, be used.

The composition disclosed herein, such as the base and/or top composition, may further comprise at least one cosmetic additive chosen from those known to persons skilled in the art as being capable of being incorporated into such a composition, such as fillers, spreading agents, wetting agents, dispersing agents, antifoams, preservatives, UV-screening agents, active agents, surfactants, moisturizing agents, perfumes, neutralizers, stabilizers and antioxidants. Of course, persons skilled in the art will be careful to choose this or these optional additional compound(s), and/or their quantity, such that the advantageous properties of the corresponding composition disclosed herein are not, or not substantially, impaired by the envisaged addition.

The invention is illustrated in greater detail in the following example, which is non-limiting in nature.

EXAMPLE a) The following polyurethane was prepared:

48.75 g (1 mol) of polytetramethylene oxide having a molecular weight of 1 400, 12.55 g (4 mol) of butanediol and 33.3 g of methyl ethyl ketone were introduced under nitrogen into a 500 ml reactor equipped with central stirring and a condenser.

The reaction medium was stirred at room temperature and then heated at the reflux temperature of the solvent for 15 minutes. 39.9 g (5.15 mol) of isophorone diisocyanate were then added dropwise over 30 minutes. The reaction was allowed to progress for 1 hour and then a mixture of 5 ml of methyl ethyl ketone and 0.1 g of tin dibutyl dilaurate was added. 60 g of methyl kethyl ketone were added and the reaction was allowed to proceed for 1 hour 10 minutes and a further 60 g of methyl ethyl ketone were added. 20 g of ethanol were then added in order to neutralize the residual isocyanate functional groups.

The polymer synthesized was precipitated from petroleum ether and then dried at 40° C. under vacuum in the presence of phosphoric anhydride.

The polymer has the following characteristics:
Number-average molecular weight: 62,426 g/mol
Polydispersity index=1.6
Glass transition temperature: −50° C. and +60° C.

b) A nail varnish having the following composition was prepared:

25 g of the polymer obtained were dissolved in 70 g of a butyl acetate/ethyl acetate 70/30 by weight mixture.

The solution obtained was then applied to the nails. A varnish film was obtained, after drying, which has the following characteristics, measured according to the protocols described above in the description:

The rate of mass loss when the film is subjected to an abrasion produced with the Taber abrasimeter at 23° C.: <0.1 mg/minute;
Loss of gloss after 1 hour: 3±1%;
Young's modulus=45±5 MPa;
Energy at break=250×10$^5$ J/m$^3$; and
Breaking strain=500±50%.

The varnish forms a film exhibiting good abrasion resistance after application to the nail.

What is claimed is:

1. A nail varnish composition comprising, in a cosmetically acceptable medium, at least one film-forming polymer that is soluble in an organic solvent in an amount greater than 90% by weight at 25° C. wherein the nail varnish composition is capable of forming a film having a rate of mass loss of less than 0.5 mg/minute when the film is subjected to abrasion produced with a Taber abrasimeter at 23° C.

2. The nail varnish composition according to claim 1, wherein the film exhibits a rate of mass loss of less than 0.2 mg/minute.

3. The nail varnish composition according to claim 2, wherein the film exhibits a rate of mass loss of less than 0.1 mg/minute.

4. The nail varnish composition according to claim 1, wherein the at least one film-forming polymer has at least a glass transition temperature ranging from −150° C. to 0° C.

5. The nail varnish composition according to claim 4, wherein the at least one film-forming polymer has at least a glass transition temperature ranging from −80° C. to 0° C.

6. The nail varnish composition according to claim 4, wherein the at least one film-forming polymer has an additional glass transition temperature ranging from greater than 0° C. to less than or equal to 150° C.

7. The nail varnish composition according to claim 6, wherein the at least one film-forming polymer has an additional glass transition temperature ranging from 10° C. to 100° C.

8. The nail varnish composition according to claim 1, wherein the nail varnish composition is capable of forming a film having a Young's modulus ranging from 10 to 200 MPa.

9. The nail varnish composition according to claim 8, wherein the nail varnish composition is capable of forming a film having a Young's modulus ranging from 10 to 100 MPa.

10. The nail varnish composition according to claim 9, wherein the nail varnish composition is capable of forming a film having a Young's modulus ranging from 10 to 50 MPa.

11. The nail varnish composition according to claim 1, wherein the nail varnish composition is capable of forming a film having a fracture energy ranging from 220×10$^5$ to 1,000× 10$^5$ J/m$^3$.

12. The nail varnish composition according to claim 11, wherein the film has a fracture energy ranging from 240×10$^5$ to 1,000×10$^5$ J/m$^3$.

13. The nail varnish composition according to claim 1, wherein the nail varnish composition is capable of forming a film having a breaking strain ranging from 300 to 2 000%.

14. The nail varnish composition according to claim 13, wherein the nail varnish composition is capable of forming a film having a breaking strain ranging from 500 to 2 000%.

15. The nail varnish composition according to claim 1, wherein the nail varnish composition is capable of forming a film having a loss of gloss, after 10 seconds of the abrasion with the Taber abrasimeter, of less than or equal to 14%, the gloss being measured before and 1 hour after the abrasion.

16. The nail varnish composition according to claim 15, wherein the nail varnish composition is capable of forming a film having a loss of gloss, after 10 seconds of the abrasion with the Taber abrasimeter, of less than or equal to 12%.

17. The nail varnish composition according to claim 16, wherein the nail varnish composition is capable of forming a film having a loss of gloss, after 10 seconds of the abrasion with the Taber abrasimeter, of less than or equal to 10%.

18. The nail varnish composition according to claim 17, wherein the nail varnish composition is capable of forming a film having a loss of gloss, after 10 seconds of the abrasion with the Taber abrasimeter, of less than 6%.

19. The nail varnish composition according to claim 1, wherein the at least one film-forming polymer is chosen from polyurethanes, polyureas, and polyurea-urethanes.

20. The nail varnish composition according to claim 1, wherein the at least one film-forming polymer is chosen from polycondensates formed by polycondensation:
of at least one diisocyanate chosen from linear and branched $C_1$-$C_{12}$ alkyl diisocyanates, $C_4$-$C_{20}$ cycloalkyl diisocyanates, and $C_6$-$C_{20}$ aryl diisocyanates;
of at least one prepolymer comprising at least two functional groups comprising at least one labile hydrogen, having a number-average molecular mass ranging from 500 to 50,000;
of at least one coupler comprising two functional groups comprising at least one labile hydrogen, having a molecular mass of less than 500.

21. The nail varnish composition according to claim 20, wherein in the at least one prepolymer, the at least two functional groups comprising at least one labile hydrogen are chosen from diols and primary and secondary diamines.

22. The nail varnish composition according to claim 20, wherein the at least one prepolymer has a number-average molecular mass ranging from 500 to 8,000.

23. The nail varnish composition according to claim 22, wherein the at least one prepolymer has a number-average molecular mass ranging from 1,000 to 3,000.

24. The nail varnish composition according to claim 20, wherein in the at least one coupler, the two functional groups comprising at least one labile hydrogen are chosen from diols, primary and secondary diamines, and amino alcohols.

25. The nail varnish composition according to claim 20, wherein the at least one coupler has a molecular mass ranging from greater than or equal to 50 to less than 500.

26. The nail varnish composition according to claim 25, wherein the at least one coupler has a molecular mass ranging from greater than or equal to 75 to less than 500.

27. The nail varnish composition according to claim 20, wherein the at least one diisocyanate is chosen from hexamethylene diisocyanate, isophorone diisocyanate, dicyclohexylmethane diisocyanate, toluene diisocyanate, diphenylmethane diisocyanate, dicyclohexylmethane diisocyanate, and tetramethylxylylene diisocyanate.

28. The nail varnish composition according to claim 20, wherein the at least one prepolymer is chosen from (poly (tetramethylene oxide))diols comprising from 10 to 80 tetramethylene oxide units; polydimethylsiloxanes comprising at least one end group chosen from ($C_2$-$C_8$)alkyleneamino ($C_2$-$C_8$)alkyl groups and $C_2$-$C_8$ ω-hydroxyalkyl groups; and hydrogenated polybutadienes comprising at least one hydroxyl end group.

29. The nail varnish composition according to claim 20, wherein the at least one prepolymer is non water-soluble.

30. The nail varnish composition according to claim 20, wherein the at least one coupler is chosen from butanediol, neopentyl glycol, amino ethanol, propylene glycol, ethylene glycol, diethylene glycol, triethylene glycol, and cyclohexanedimethanol.

31. The nail varnish composition according to claim 20, wherein the at least one prepolymer and the at least one coupler are present in the at least one film-forming polymer in an amount such that the prepolymer/coupler molar ratio ranges from 1:1 to 1:5 and the (prepolymer+coupler)/diisocyanate molar ratio ranges from 0.9:1 to 1.1:1.

32. The nail varnish composition according to claim 31, wherein the at least one film-forming polymer is chosen from polyurethanes.

33. The nail varnish composition according to claim 20, wherein the at least one film-forming polymer is such that the at least one prepolymer, the at least one diisocyanate, and the at least one coupler are present in the at least one film-forming polymer in the following molar proportion:
the at least one prepolymer: 1;
the at least one diisocyanate: from 2 to 6; and
the at least one coupler: from 1 to 5.

34. The nail varnish composition according to claim 20, wherein when the (prepolymer+coupler)/diisocyanate molar ratio is less than 1, the free isocyanate groups are blocked by reaction with at least one compound comprising at least one labile hydrogen.

35. The nail varnish composition according to claim 34, wherein the at least one compound comprising at least one labile hydrogen is ethanol.

36. The nail varnish composition according to claim 1, wherein the at least one film-forming polymer has a number-average molecular weight of less than or equal to 300,000.

37. The nail varnish composition according to claim 36, wherein the at least one film-forming polymer has a number-average molecular weight ranging from 10,000 to 150,000.

38. The nail varnish composition according to claim 1, wherein the at least one film-forming polymer is present in an amount ranging from 0.1% to 60% by weight, relative to the total weight of the composition.

39. The nail varnish composition according to claim 38, wherein the at least one film-forming polymer is present in an amount ranging from 0.1% to 40% by weight, relative to the total weight of the composition.

40. The nail varnish composition according to claim 1, further comprising at least one additional film-forming polymer chosen from sulphonamide resins, alkyd resins, and cellulose esters.

41. The nail varnish composition according to claim 1, further comprising at least one plasticizing agent.

42. The nail varnish composition according to claim 1, comprising at least one organic solvent medium.

43. The nail varnish composition according to claim 42, wherein the at least one organic solvent medium is anhydrous.

44. The nail varnish composition according to claim 42, wherein the at least one organic solvent medium comprises at least one organic solvent chosen from ketones, alcohols, glycols, propylene glycol ethers, short-chain esters, ethers, alkanes, aromatic cyclic compounds, and aldehydes.

45. The nail varnish composition according to claim 1, comprising at least one aqueous medium.

46. The nail varnish composition according to claim 1, comprising at least one cosmetic additive chosen from thickening agents, coloring matters, fillers, spreading agents, wetting agents, dispersing agents, antifoams, preservatives, UV-screening agents, active agents, surfactants, moisturizing agents, perfumes, neutralizers, stabilizers and antioxidants.

47. A cosmetic method for making up and/or non-therapeutic care of nails, comprising applying to the nails at least one layer of nail varnish comprising, in a cosmetically acceptable medium, at least one film-forming polymer that is soluble in an organic solvent in an amount greater than 90% by weight at 25° C., wherein the nail varnish is capable of forming a film having a rate of mass loss of less than 0.5 mg/minute when the film is subjected to abrasion produced with a Taber abrasimeter at 23° C.

* * * * *